(12) United States Patent
Sakai

(10) Patent No.: US 6,495,142 B2
(45) Date of Patent: Dec. 17, 2002

(54) METHODS FOR TREATMENT OF IMPULSE CONTROL DISORDERS

(75) Inventor: Kazuo Sakai, Twin Palace 603, 2-34-8 Sendagi, Bunkyo-ku, Tokyo (JP)

(73) Assignees: Kazuo Sakai, Tokyo (JP); Kitosan Food Industry Co., Ltd., Osaka (JP)

( * ) Notice: Subject to any disclaimer, the term of this patent is extended or adjusted under 35 U.S.C. 154(b) by 0 days.

(21) Appl. No.: 09/804,226

(22) Filed: Mar. 13, 2001

(65) Prior Publication Data

US 2002/0052339 A1 May 2, 2002

(30) Foreign Application Priority Data

Sep. 13, 2000 (JP) .......................... 2000-278183

(51) Int. Cl.$^7$ .......................... A61K 47/00; A01N 37/18
(52) U.S. Cl. .................. 424/195.16; 424/439; 514/55; 514/810
(58) Field of Search .................. 424/195.16, 725, 424/439; 510/810; 514/810, 909, 55

(56) References Cited

U.S. PATENT DOCUMENTS 4,363,801 A * 12/1982 Nagyvary

FOREIGN PATENT DOCUMENTS

| JP | 54-148890 | 11/1979 |
|----|-----------|---------|
| JP | 56-33401 | 8/1981 |
| JP | 363307826 | * 12/1988 |
| JP | 04018036 | * 1/1992 |
| JP | 6-81763 | 10/1994 |
| JP | 2547153 | 8/1996 |
| JP | 05316967 | * 10/1996 |
| WO | 05316967 | * 10/1996 |

OTHER PUBLICATIONS

Sawayaka Genki, vol. 73, No. 8, Aug. 2000.
Shukan Gendai, vol. 42, May 2000.
Nikkan Gendai, vol. 7101, No. 14, Mar. 2000.
Daijyoubu, vol. 62, No. 5, May 2000.

* cited by examiner

*Primary Examiner*—Christopher R. Tate
*Assistant Examiner*—Michele C. Flood
(74) *Attorney, Agent, or Firm*—Oblon, Spivak, McClelland, Maier & Neustadt, P.C.

(57) ABSTRACT

Methods of treating, and/or improving impulse control disorder, which comprises administering to a living subject, a composition comprising chitosan as an effective ingredient, having a weight-average molecular weight of 80,000 to 100,000 and a number-average molecular weight of 30,000 to 40,000, as measured by gel permeation chromatography (GPC). Also provided are methods for giving an activity of repressing impulse to food products and drinks by putting said chitosan in the food products, drinks and the material therefor.

12 Claims, No Drawings

METHODS FOR TREATMENT OF IMPULSE CONTROL DISORDERS

BACKGROUND OF THE INVENTION

1. Field of the Invention

The present invention relates to a method for treating, improving or preventing impulse control disorder, by administering a composition comprising a specified low-molecular weight chitosan and/or a derivative thereof to a living subject, particularly to a subject suffering from an impulse control disorder. In addition, a drug, a food product including a health food product, and a drink containing the chitosan is also provided by the present invention.

2. Description of the Background

Depression and Bulimia are common psychiatric diseases in the stressful current society, and many people suffer from these disorders. Until now, drugs such as anti-depression drugs including selective serotonin reuptake inhibitor (SSRI) have been used for treatment of these diseases. However, these drugs cause many side effects and cannot be used safely for children and aged people. Even if adults take the drugs, they must endure many side effects therefrom.

Recently, the frequency of crimes committed by teen-agers has been increasing. Such children evidencing aggressive behavior often commit violence in their schools and/or families, and the collapse of the school and the family as social structures is the serious problem in society. These children are affected by a syndrome of impulse control disorder, including borderline personality disorder, emotionally unstable personality disorder, conduct disorder, defiant personality disorder, explosive personality disorder, intermittent explosive disorder, etc. Tranquilizers used for treatment of these children cause side effect such as sleepiness all day long and lack of motivation for study and every day life.

It has been pointed out that the aggressive behavior of those children was due to the lack of discipline or irregular dietary regimen at home. However, no effective health food for impulse control disorder has been reported to date.

Chitosan is a polysaccharide which has the chemical structure of β-1,4-poly-D-glucosamine and is produced by deacetylation of chitin, which is contained in the shell of the Crustacea such as crabs and lobsters. It is soluble in diluted acid solution but insoluble in water. It is not digested by digestion enzymes in humans, and, therefore, it is one of the dietary fibers. To date, it has been used for flocculants in waste water treatment, cosmetics, artificial skin, cationic resins, plant activating agents, and food materials. Recently it was discovered that chitosan showed physiological functions in humans, such as improvement of cholesterol levels in blood, inhibition of lipid absorption, anti-hypertension, and improvement of intestinal metabolism. Nevertheless, no mental effects produced by chitosan have been described.

Chitosan is a high-molecular weight polymer in nature, insoluble in water and alcohol, slightly soluble in diluted acid solution, and it is difficult to make highly concentrated solutions of chitosan due to the high viscosity because of its high molecular weight. To overcome this problem, there are many known methods to produce low-molecular weight chitosan of lower viscosity and higher solubility. For example, the low-molecular weight chitosan having various and arbitrary molecular weight can be produced by treating chitosan obtained by deacetylation of natural chitin, with 0.007 to 0.35% hydrogen peroxide solution adjusted at pH 6 to 12, in Japanese Patent Kokoku Publication JP-B-56-33401.

SUMMARY OF THE INVENTION

It is an object to the present invention to provide a method for treating, improving and/or preventing impulse control disorder.

It is also an object of the present invention to provide a method for treating, improving and/or preventing impulse control disorder by administering a highly safe drug which may be in the form of a food, such as a health food product or a drink.

Recognizing the importance of providing novel methods useful in the therapy of impulse control disorders, the present inventor has investigated the effects of many drugs and health foods for the treatment of impulse control disorder.

These efforts led to the discovery that a low-molecular weight chitosan which has a specified molecular weight, shows excellent effect for improving impulse control disorder.

Accordingly, the present invention provides a method for treating, improving and/or preventing impulse control disorder, which comprises administering or giving to a living subject, particularly to a patient suffering from such diseases as impulse control disorders, a composition comprising chitosan as an effective ingredient, having a weight-average molecular weight of approximately 80,000 to 100,000 and/or a number-average molecular weight of approximately 30,000 to 40,000, as measured or determined by Gel Permeation Chromatography (GPC). The chitosan may be in the form of salt. The chitosan can be in the form of a pharmaceutically acceptable salt, an edible salt or a derivative converted to free chitosan in vivo.

The present invention is not limited to the type of impulse control disorder. Impulse control disorders include, but are not limited to, borderline personality disorder, obsessive-compulsive personality disorder, emotionally unstable personality disorder, defiant personality disorder, conduct disorder, explosive personality disorder, intermittent explosive disorder, bulimia, excessive sexual impulse and compulsive buying.

The composition may in the form of drug, food product or drink. In a preferred embodiment, the chitosan used for the composition in the present invention has a weight-average molecular weight of approximately 85,000 to 95,000 when measured by GPC. In a further preferred embodiment, the composition also comprises an edible organic acid and/or an amino acid. Thus, the chitosan is soluble in water and absorbed easily via oral administration.

Although the functional mechanism of the effect is not known, and without being limited by any particular theory, it is speculated that the chitosan may stimulate the parasympathetic nerves or interact with the neurotransmitters in brain by an unknown mechanism. This theory, of course, does not restrict the scope of the present invention.

It is another object of the present invention is to provide methods for imparting an activity of repressing impulse to a food product or a drink by combining with the food product, drink or the materials (precursors) therefor, chitosan having a weight-average molecular weight of approximately 80,000 to 100,000 and a number-average molecular weight of approximately 30,000 to 40,000, as measured or determined by GPC.

Thus, the present invention also provides a method of imparting an ability to repress impulses to a food product or a drink, comprising combining the food product or the drink with chitosan having a weight-average molecular weight of 80,000 to 100,000 and a number-average molecular weight of 30,000 to 40,000 as measured by GPC.

Thus, according to the method of the present invention, the symptom of the impulse control disorder for which the treatment by the conventional drugs as anti-schizophrenia drug, etc., is ineffective, can be improved greatly without any side effects.

Therefore, the effective ingredient in the composition of the present invention, i.e., the chitosan, can be used not only as the drug for impulse control disorder, but also as food products and drinks such as health food products for unsymptomatic subjects.

A more complete appreciation of the invention and many of the attendant advantages thereof will be readily obtained as the same becomes better understood by reference to the following detailed description.

DETAILED DESCRIPTION OF THE INVENTION

The chitosan used in the present invention as an active ingredient has a defined molecular weight, and can be produced by the method, for example, described in Japanese Patent Kokoku Publication JP-B-56-33401, incorporated herein by reference. The molecular weight of chitosan as a macromolecular compound, can be estimated by the correlation between the viscosity of the solution and the molecular weight. When chitosan is processed to low-molecular weight form, the molecular weight generally ranges in an interval, and the molecular weight measured by viscosity of the solution indicates only the average molecular weight. Moreover, it is well-understood by the person skilled in the art that different methods of measuring molecular weight give different results. Thus, the molecular weight of the low-molecular weight chitosan is measured or determined by GPC (Gel Permeation Chromatography), equipped with an HPLC apparatus.

The effective ingredient of the composition used in the present invention may be used in a free form of chitosan, a salt form, or the derivatives thereof. A pharmaceutically acceptable salt of the chitosan is preferably employed. The specific form of salt includes, but is not limited to the type of salt to form an acid addition salt, usually used an acid such as hydrochloric acid, hydrobromic acid, sulfuric acid, phosphoric acid, formic acid, acetic acid, fumaric acid, maleic acid, malic acid, tartaric acid, lactic acid, glutamic acid, etc. In a preferred embodiment, the chitosan having a weight-average molecular weight of 80,000 to 100,000 and a number-average molecular weight of 30,000 to 50,000, when measured by GPC, is dissolved in the solution of, more preferably, an edible organic acid(s) or an amino acid(s). The edible organic acid is one such as vinegar, lactic acid, malic acid, ascorbic acid etc., and the amino acid is for example, acidic amino acid (L-glutamic acid, etc.). Various derivatives such as esters converted to the free chitosan in the living body, are also included in the definition of the effective ingredient of the composition.

The range for the weight-average molecular weight of the chitosan described above includes all specific values and subranges therebetween, such as 85,000; 90,000; and 95,000.

The range for the number average molecular weight of the chitosan described above includes all specific values and subranges therebetween such as 35,000; 40,000; and 45,000.

In a preferred embodiment of the present invention, Red koji extracts are included in the composition with aforementioned edible organic acid(s) or amino acid(s). These additives enable the chitosan to be soluble in water with higher concentration. Moreover, when the composition including the chitosan is used as a food product or an orally ingestible form such as drinks, the Red koji extracts suppresses the bitter taste of the chitosan and enhances the dissolution and absorption after eating or drinking.

The composition containing the chitosan can be administered or given in a conventional administration form or eatable form, for example, in the form of granules, tablets, capsules, syrups, suspensions, etc. for oral administration or eating. Preferably, the composition is used in the form of tablets. The tablets can be prepared by mixing the effective ingredient with a conventional carrier, diluent, binder, stabilizer, food additives, etc., if necessary. Preferably, it is prepared in the form of tablets by adding lactic acid, sucrose ester, calcium phosphate, L-valine, wax, dextrin, etc., to the composition. A particularly suitable preparation for improving impulse control disorder, is commercially available as "Mindace" ("Mindace" is the trademark for a health food product which is manufactured by KITOSAN FOOD INDUSTRY Co. Ltd., Japan.)

The subject to be treated by the present invention is not limited to one suffering from impulsive control disorder. Mammals, especially human beings, are a typical subject. As used herein, the term "impulsive control disorder" refers to those provided in the Diagnostic and Statistical Manual (DSM IV), American Psychological Association (APA). These impulsive control disorders include, but are not limited to, borderline personality disorder, emotionally unstable personality disorder, defiant personality disorder, conduct disorder, explosive personality disorder, intermittent explosive disorder, bulimia, excessive sexual impulse and compulsive buying. Borderline Personality Disorder (BPD) is a severe, chronic, disabling, and potentially lethal psychiatric condition. Subjects who suffer with this disorder have extreme and long standing instability in their emotional lives, as well as in their behavior and their self-image. These instabilities of emotion, behavior, and self-image have devastating and sometimes deadly consequences. Subjects with BPD have repeated and frequent difficulties in their relationships and work lives and they feel alternating extremes of anger, depression, and emptiness. These symptoms may be caused by uncontrollable impulses. Bulimia may be caused by excess of an impulse of appetite. Compulsive buying may be caused by an excess of materialistic desires.

The present invention has the same or more effectiveness, in view of reducing the impulse and side effects, as compared to known methods using the drugs available in the Japanese and American market, and described in detail in Examples below. A summary of the clinical data for the present invention is as follows.

At present, there are three types of drugs for treating the patient suffering from over-impulse disorder, such as (1) anti-schizophrenia drugs, (2) anti-epilepsy drug, and (3) anti-manic drugs. These drugs are approved as a drug for schizophrenia, epilepsy and manic disorder, respectively. In addition, they are used for a person who injures other people by impulsive behavior, destroys the object or continues to injure by himself, even if the diagnosis of the person is not fixed. It is common to try to suppress the impulse by combining two or three types of the above drugs in several amounts, if a single drug is not effective.

Twelve cases of impulse control disorder, which have been treated at Stress-care Hibiya Clinic, and not effective for the violence and self-injury by treating with drugs above (1) to (3) or combination thereof, are treated by the method of the present invention. When 20 to 40 tablets of the chitosan (approximately 1,300 to 2,800 mg as an effective ingredient) are orally administered, all cases showed improvement. There was no side effect. In three cases out of twelve, the effect of the present invention was confirmed without the use of drugs of (1) to (3), which have side effects as described above.

The dosage and the administration frequency of the effective ingredient of the composition vary according to the conditions, ages, weights of the patients, or the administration forms, but the effective ingredient of the composition is administered in a dose of approximately 1 to 3000 mg/day/adult, preferably in a dose of approximately 100 to 2000 mg/day/adult as the amount of the chitosan, for oral administration. These ranges include all specific values and subranges therebetween, such as 2.5, 10, 25, 50, 75, 200, 500, 1,000, 1,500, and 2,500 mg/day/adult.

The chitosan as an effective ingredient of the present invention is one of the components of cell wall of Zygomycetes and foods produced by using the microorganisms have been eaten by human for many years. Moreover, a large quantity of chitosan has been used for the past ten years or more as a raw material for health food, thus, the low-molecular weight chitosan is also supposed to be highly safe material as drugs or food products.

When the effective ingredient of the composition is put into food products or drinks, the activity of repressing impulse can be imparted to the food products and drinks or those under production thereof. In a preferred embodiment, edible organic acids or amino acids are used for dissolving the effective ingredient. By consuming these foods and drinks, the mental condition of the subject can be highly tranquil. Thus, it is useful for improving and/or preventing a subject susceptible to impulse control disorder that the food products and drinks containing the effective ingredient of the composition are eaten as a health food.

The content of the effective ingredient in the composition in the form of food products and drinks vary according to the form of the foods and drinks, etc. For example it can be contained in the form of granules, tablets, capsules, syrups, suspensions, etc. in a dose of approximately 1 to 3000 mg/day/adult, preferably in a dose of approximately 100 to 2000 mg/day/adult as the effective ingredient. These ranges include all specific values and subranges therebetween, such as 2, 5, 10, 25, 50, 75, 200, 500, 1,000, 1,500, and 2,500 mg/day/adult.

EXAMPLES

Having generally described this invention, a further understanding can be obtained by reference to certain specific examples which are provided herein for purposes of illustration only and are not intended to be limiting unless otherwise specified.

Example 1

Preparation of Specified Low-molecular Weight Chitosan 300 kg of dried flaky chitin were suspended in 7 m$^3$ of aqueous solution of 48% caustic soda and stirred at 90° C. for 14 hours to make chitosan by deacetylation of chitin. After removing the alkaline solution and washing with water, the resulting matters were suspended in 6 m$^3$ of water. The pH value of the suspension was 10.3. Then, 4 kg of hydrogen peroxide solution were added to the suspension heated at 60° C., and a treatment for reducing the molecular weight of chitosan was performed at the same temperature. After two and four our incubations respectively, each 2 kg of hydrogen peroxide was further added, and a treatment of total 6 hour incubation was performed for reducing the molecular weight of the chitosan. Then, the reaction mixture was treated by catalase to remove the residual hydrogen peroxide, washed with water, dried and crushed to obtain chitosan powder (150 kg). To the powder, acetic acid in the same quantity by weight base as the powder were added, and then water were added to dissolve the same and 1% by weight of aqueous solution of chitosan were prepared. The viscosity of the solution showed 7 mPa·s by measuring with a rotational viscometer under the temperature kept at 20° C.

Example 2

Measurement of Molecular Weight by GPC

Molecular weight of low-molecular weight chitosan prepared in the Example 1 was measured by the following analysis condition.

| | |
|---|---|
| Column: | Shodex Ohpak SB-G + SB-805HQ + SB-806HQ |
| Mobile phase: | 0.5 M acetic acid/0.5 M Sodium acetate buffer |
| Flow rate: | 1.0 mL/min |
| Temperature: | 40° C. |
| Detector: | RI (Reflex Index) |
| Sample concentration and sample volume: | 0.05%, 200 µL |

For molecular weight calibration, standard pullulan samples (Shodex Pullulan P-5, P-10, P-20, P-50, P-100, P-200, P-400, P-800 and P-1600 each corresponding to molecular weights of 5,900, 11,800, 22,800, 47,300, 112,000, 212,000, 404,000, 788,000 and 1,600,000, respectively) and chitohexaose (molecular weight 1,203) were used.

The result of the calculated molecular weight of the low-molecular weight chitosan prepared above was 88,100 as a weight-average molecular weight and 34,500 as a number-average molecular weight.

Example 3

Preparation of Dried Powder-1

2 kg of chitosan prepared in the Example 1, of which the molecular weight was measured in the Example 2, was mixed with 8 kg of water to give a suspension of the chitosan. To this suspension, 1 kg of lactic acid was added, and the mixture was stirred for 30 minutes to dissolve the chitosan. The concentration of chitosan in this solution was 19% by weight base, when it was measured by the colloidal titration method, and the viscosity of the solution was 6,000 mPa·s.

The solution was filtered to remove impurities, and thus obtained filtrate was diluted with 30 kg of aqueous solution in which 5 kg of dextrin was dissolved, and dried with spray dryer to obtain a dried powder. The yield of the dried powder was 7.5 kg and the concentration of chitosan was 43%.

Preparation of Dried Powder-2

The chitosan solution produced as above (Concentration: 19%, Viscosity:6,000 mPa·s) was diluted with 30 kg of water and dried with the spray dryer. In this case, the yield of the dried powder was 2.5 kg and the concentration of chitosan was 83%.

Example 4
Preparation of Tablet/Capsule
Tablets were prepared from the following components.

| Components | Amount (g) |
|---|---|
| Dried powder-1 of Example 3 | 5000 |
| L-Valine | 26 |
| Wax | 9.5 |
| Total | 5035.5 |

Each component was mixed together, and tabletted to give tablets. The content of the chitosan in the tablet was 42%.

Preparation of Capsule
Capsules were prepared from the following components.

| Components | Amount (g) |
|---|---|
| Dried powder-1 of Example 3 | 2000 |
| L-Valine | 10 |
| Wax | 4 |
| Total | 2014 |

Each component was mixed together, and packed in the capsule. The content of the chitosan in the total powder of the capsule was 82%.

Example 5
Treatment of Borderline Personality Disorder

A twenty-five year old man without occupation for long time, who stayed in doors and continued to use violence towards his parents. To seek treatment, he visited the inventor's clinic. Treatment with several kind of medicine had not been effective, then he was put into a mental hospital for preventing immediate violence. He was diagnosed as severe borderline personality disorder and discharged from the hospital after 2 months due to the lack of response to treatment. After administration of 30 tablets/day of chitosan (2000 mg) prepared in the example 4 (the preparation of tablet), his impulsive symptoms decreased significantly, the violence towards his parents had disappeared and his symptoms have been stable.

Example 6
Treatment of Conduct Disorder

A seventeen year old man had a history of mental retardation. In recent adolescent ages showing severe sexual impulse, he presented exhibitionism symptoms and impulsive violence for unspecified person and his mother. His symptoms had been refractory to treatments including (1) anti-schizophrenia drug, (2) anti-epilepsy drug, and (3) anti-manic drug in large amounts. On the contrary, he developed dizziness and allophasis as side effects without any suppression of the impulse, and he had problems in daily life. After administration of 20 tablets/day of chitosan (1,300 mg) prepared in Example 4 (the preparation of tablet), his exhibitionism symptoms were cured and he stopped to conduct the violence for unspecified person. Moreover, social techniques such as getting on the bus by himself or going to the destination and coming back, were advanced and adaptability to society greatly increased by the observation of his mother and teacher. It was decided that the increase of the social techniques was due to the suppression of the impulse of the patient.

Example 7
Treatment of Bulimia and Compulsive Buying

A thirty-one year old woman visited the inventor's clinic, and reported the history of cutting her own wrist, bulimia, compulsive buying and uncontrolled sexual impulse for men since the age of seventeen. These symptoms had been refractory to treatments provided by any drugs or any combination of drugs including (1) anti-schizophrenia drug, (2) anti-epilepsy drug, and (3) anti-manic drug. When 40 tablets/day of the chitosan (2,800 mg) prepared in the example 4 (the preparation of tablet) were applied to her, all impulses such as the impulse to suicide, the sexual impulse to male, impulses to shopping and over-eating were tolerated. She has returned to a healthy social life.

This application is based on Japanese Patent Application No.2000-278183, filed on Sep. 13, 2000, which is expressly incorporated herein by reference in its entirety.

What is claimed is:

1. A method for treating and/or improving an impulse control disorder, comprising
administering to a living subject in need thereof, a composition consisting essentially of an effective amount of chitosan,
wherein said chitosan has a weight-average molecular weight of 80,000 to 100,000 and a number-average molecular weight of 30,000 to 40,000 as measured by gel permeation chromatography.

2. The method of claim 1, wherein the chitosan is in the form of salt.

3. The method of claim 1, wherein the chitosan is not in the form of salt.

4. The method of claim 1, wherein the chitosan is in the form of a pharmaceutically acceptable salt or an edible salt.

5. The method of claim 1, wherein the chitosan has a weight-average molecular weight of 85,000 to 95,000.

6. The method of claim 1, wherein the composition further comprises an edible organic acid and/or an amino acid.

7. The method of claim 6, wherein the composition further comprises Red koji extract.

8. The method of claim 1, wherein the composition further comprises Red koji extract.

9. The method of claim 1, wherein the impulse control disorder is selected from the group consisting of borderline personality disorder, emotionally unstable personality disorder, defiant personality disorder, conduct disorder, explosive personality disorder, intermittent explosive disorder, bulimia, excessive sexual impulse, and compulsive buying.

10. The method of claim 1, wherein the composition is in the form of a granule, a tablet, or an orally ingestible form.

11. The method of claim 1, wherein the composition is in the form of a drug, a food product, or a drink.

12. The method of claim 11, wherein the food product is a health food.

* * * * *